United States Patent [19]

Lysons

[11] Patent Number: 4,748,019
[45] Date of Patent: May 31, 1988

[54] VACCINE FOR SWINE DYSENTERY

[75] Inventor: Richard J. Lysons, Reading, England

[73] Assignee: National Research Development Corporation, London, England

[21] Appl. No.: 789,960

[22] PCT Filed: Mar. 4, 1985

[86] PCT No.: PCT/GB85/00087

§ 371 Date: Oct. 9, 1985

§ 102(e) Date: Oct. 9, 1985

[87] PCT Pub. No.: WO85/03875

PCT Pub. Date: Sep. 12, 1985

[30] Foreign Application Priority Data

Mar. 2, 1984 [GB] United Kingdom ................. 8405530

[51] Int. Cl.$^4$ .......................... A61K 39/02; C12N 1/20
[52] U.S. Cl. ........................................ 424/92; 424/88
[58] Field of Search .......................... 429/92; 424/88

[56] References Cited

U.S. PATENT DOCUMENTS

| 4,100,272 | 7/1978 | Glock et al. ........................... 424/92 |
| 4,152,413 | 5/1979 | Goodnow .......................... 424/92 X |
| 4,152,414 | 5/1979 | Harris et al. ...................... 424/92 X |
| 4,152,415 | 5/1979 | Harris et al. ...................... 424/92 X |
| 4,469,672 | 9/1984 | Harris ............................... 424/92 X |

FOREIGN PATENT DOCUMENTS 9577A   4/1980   European Pat. Off. .

OTHER PUBLICATIONS

M. J. Hudson et al., Res. Vet. Sci. 21, 366–367 (1976).
R. M. Lemcke et al., Res. Vet. Sci. 26, 315–319 (1979).
R. M. Lemcke et al., J. General Microbiology 116, 539–543 (1980).
R. J. Lysons et al., Proceedings of the 2nd International Symposium of Veterinary Laboratory Diagnosticians, Lucerne, 1980, pp. 118–120.
R. J. Lysons et al., Proceedings of the International Pig Veterinary Society Congress, Mexico City 1982, p. 40.
R. M. Lemcke et al., Proceedings of the International Pig Veterinary Society Congress, Mexico City 1982, p. 39.
J. F. L. Pohlenz et al., Proceeding of the 3rd International Symposium of Veterinary Laboratory Diagnosticians, Ames, Iowa, 1983, pp. 553–558.
M. R. Burrows et al., Vet. Rec., 108, 187–189 (Feb. 28, 1981).
F. J. Bourne et al., Pig News and Information 2, 141–144 (1981).
Y. Inaba et al., Archiv fur die gesamte Virusforschung 44, 121–132 (1974).
N. F. Pierce and J. L. Gowans, J. Exp. Med. 142, 1550–1563 (1975).
L. D. Bloom et al., Australian J. Exp. Biol. Med. Sci., 57, 313–323 (1979).
S. Nakashima et al., J. Biochem. 79, 1323–1330 (1976).
J. S. Mackenzie et al., J. Hyg. Camb. 80, 21 (1978).
R. Thomssen, Monogr. Allergy, 9, 155–176 (Karger, Basel 1975).
M. Duchet-Suchaux et al., Ann. Rech. Vet. (France) 14, 319–331 (1983).
R. A. McDonald et al., Federation Proceedings (43)(3), abstract No. 562 (1974).
D. F. Keren et al., Infection and Immunity 31, 1193–1202 (1981).
D. F. Keren et al., Federation Proceedings 41(3), Abstract No. 3261 (1982).
D. F. Keren et al., Infection and Immunity 42 202–207 (1983).
N. F. Pierce et al., Infection and Immunity 21, 185–193 (1978).
A. J. Husband and M. J. Bennell, Pig News and Information 1, 211–213 (1980).
A. J. Husband and J. T. Seaman, Australian Veterinary Journal, 55, 435–436 (1979).
L. A. Joens, U. S. Livestock Conservation Institute, Proceedings, 1986, pp. 161–169.

*Primary Examiner*—Howard E. Schain
*Attorney, Agent, or Firm*—Murray and Whisenhunt

[57] ABSTRACT

Existing vaccines against swine dysentery are not very effective. It has now been found that an effective regime of vaccination comprises administering parenterally to pigs a priming dose of killed virulent or pathogenic *T. hyodysenteriae* effective to stimulate the immune response of the pig to a subsequent dose of a live avirulent or non-pathogenic strain of *T. hyodysenteriae* and at about the same time or thereafter administering this live strain orally. The invention provides a kit for use in such a method. The live strain is preferably NCTC 11628 deposited as a Budapest Treaty patent deposit.

12 Claims, No Drawings

VACCINE FOR SWINE DYSENTERY

BACKGROUND OF THE INVENTION

1. Field of the Invention

This invention relates to a vaccine for swine dysentery.

2. Description of the Prior Art

It is recognised that pigs which have recovered from swine dysentery (SD) eventually become immune to subsequent challenge. However, to be solidly resistant they must have recovered without the aid of antibiotic treatment. This implies that prolonged and intensive antigenic stimulation at the surface of the large intestine is necessary to produce immunity. The poor degree of protection afforded by current vaccines suggests that such stimulation is difficult to mimic artificially.

U.S. Pat. No. 4,100,272 (R. D. Glock et al.) describes a swine dysentery vaccine of killed cells of a virulent (pathogenic) isolate of *Treponema hyodysenteriae*, for parenteral administration. The isolate must be virulent: attenuated or nonvirulent isolates are said not to be desirable. Two isolates are disclosed by deposition in the ATCC under Nos. 31212 and 31287.

U.S. Pat. No. 4,152,413 (R. A. Goodnow) describes a swine dysentery vaccine of killed cells of a virulent isolate of *Treponema hyodysenteriae*, for oral administration. The isolates must be virulent: attenuated or nonvirulent isolates are said not to be desirable. The same two isolates as above are disclosed for the oral vaccine. The specification recommends dosing the pigs with the oral vaccine every day for 5 days, or a "combination procedure" believed to enhance the effectiveness of the oral administration. The procedure involves a previous administration of the same vaccine parenterally, e.g. subcutaneously or intraperitoneally. Such a procedure is described in more detail in U.S. Pat. No. 4,152,415 (D. L. Harris et al.).

All the above U.S. Patents relate exclusively to killed vaccines and emphasise the requirement that the strain be virulent. Other virulent (pathogenic) strains have been used experimentally in killed vaccines.

An avirulent variant of *Treponema hyodysenteriae* has been isolated from herds with no history of SD. This isolate administered orally to susceptible pigs did not produce clinical symptoms of disease or afford protection against subsequent challenge with a virulent (pathogenic) strain (P18A) of *T. hyodysenteriae*. See R. J. Lysons (the present inventor) et al., Proceedings of the International Pig Veterinary Society Congress, 1982, page 40. None of these isolates was made publicly available.

SUMMARY OF THE INVENTION

It has now been found that when oral administration of an avirulent (non-pathogenic) variant strain is caused to be preceded physiologically by parenteral administration of a killed vaccine, pigs can be successfully immunised against SD.

The basis of the present invention is that parenteral administration of the killed vaccine in some way serves to "prime" the animal to recognise the live antigenic avirulent strain administered orally. Accordingly, where relevant national patent law allows, the invention provides a method of treatment of swine dysentery in pigs which comprises administering parenterally to pigs at least one priming dose of killed virulent (pathogenic) *T. hyodysenteriae* effective to stimulate the immune response of the pig to a subsequent dose of a live avirulent (non-pathogenic) strain of *T. hyodysenteriae* and at about the same time or thereafter administering orally to the pigs at least one said dose of the live strain effective to immunise the pigs against swine dysentery. The live avirulent strain is preferably the VS1 strain described above.

The preferred avirulent strain is designated herein "VS1" and has been deposited on Feb. 8, 1984 for patent purposes in a culture collection under the regulations of the Budapest Treaty on the International Recognition of the Deposit of Microorganisms for the Purposes of Patent Procedure, as NCTC 11628. References herein to "VS1" are to be construed as references to the strain of *Treponema hyodysenteriae* so deposited.

The invention provides the VS1 strain per se, as well as avirulent (non-pathogenic) mutants and variants thereof. It includes also a biologically pure culture thereof.

The invention further includes a kit for use in a regime of vaccination as defined above, comprising a first component comprising a killed virulent (pathogenic) strain of *T. hyodysenteriae* and a second component comprising a live, non-pathogenic strain of *T. hyodysenteriae* or of a mutant or variant thereof, said strain being preferably VS1. Each component may be formulated together with an adjuvant or carrier.

DESCRIPTION OF THE PREFERRED EMBODIMENTS

VS1 was isolated from pigs in each of 3 herds kept on separate farms and known to be free of swine dysentery. The herds had a common source of breeding stock. It is considered to be a variant strain of the usual strains of *T. hyodysenteriae*. It was very difficult to locate. When 187 pigs were tested, 103 of them possessed spirochaetes but in only 3 of them could isolates of *Treponema hyodysenteriae* be obtained. VS1 is indistinguishable from typical virulent strains of *T. hyodysenteriae* strains when subjected to standard serological tests for the identification of *T. hyodysenteriae*, e.g. the fluorescent antibody test, the slide agglutination and the disc-growth inhibition tests. In view of the difficulty of obtaining and identifying an avirulent variant strain of *T. hyodysenteriae*, it follows that deposit of the strain is required to provide an enabling disclosure whereby the man skilled in the art could make use of the present invention.

The VS1 strain has been found to be highly persistent, there being a 2½ year interval between the first and last of the three isolates. Moreover the organism showed no tendency to revert to pathogenicity. In the 3 herds there have been more than 100,000 pigs exposed to this organism since first recognition of its presence, but no swine dysentery was observed.

The killed virulent strain is conveniently P18A. This strain has been deposited as a scientific (open) deposit as NCTC 11615. Other killed virulent strains of *T. hyodysenteriae* will give acceptable results in the regime of vaccination. Thus, for example the killed strain could be ATCC strain 31212 or 31287—see U.S. Pat. Nos. 4,152,413 and 4,152,415.

Preferably the killed component is formulated with an adjuvant. Adjuvants tried experimentally are (1) oil adjuvants which are mixtures of a white mineral oil ("Marcol 52") with a mannide monooleate ("Arlacel A"), (2) aluminium hydroxide gel ("Alhydrogel") and (3) saponin. The oily adjuvant (1) caused abcesses and is therefore not recommended. Adjuvants (2) and (3) did not cause any tissue reactions.

The parenteral administration can be carried out in any conventional way appropriate for vaccination of pigs with killed vaccine, e.g. subcutaneously, intraperitoneally or (preferred) intramuscularly.

In a preferred way of carrying out the regime of vaccination the killed strain is administered intraperitoneally or intramuscularly in two doses, at intervals, for example of 3 weeks or more. The oral administration is preferably made in one dose. Preferably at least 5 days and most preferably at least 8 days should elapse between the parenteral dose or the first parenteral dose if there is more than one (as is preferred) and the beginning of oral dosing. The oral administration might take the form of two or more doses given at intervals.

The oral dose or the first oral dose could be given at the same time as the first parenteral dose bearing in mind that the live organism will take some days to colonise the large intestine of the pig, thus enabling the parenterally administered organism time to have the desired physiologically precedent priming effect.

The avirulent strain can conveniently be administered as a culture. It could be on a solid medium, such as an agar, but is preferably a liquid culture, which can be refrigerated for storage. It is then conveniently administered by holding the pig and squirting the culture down its throat. An excipient, carrier or diluent could of course be added to the culture if desired.

The invention will ordinarily be applied to young pigs, which can be weaned pigs or suckling pigs. Preliminary results suggest that it is more effective for weaned pigs.

The VS1 strain of the invention is also useful in that it may help identify genes coding for at least one potential antigenic determinant region characteristic of virulent *T. hyodysenteriae* DNA. By hybridisation techniques and DNA sequencing it will then be possible to identify this region, a step which will assist in the production of protective antigens, e.g. polypeptides either synthetically or by another organism. Alternatively an organism could be genetically manipulated to contain DNA which codes for and would express protective antigens. This organism could be used as a live vector in place of VS1.

Full details of the characteristics of VS1 and P18A are provided in the following section:

CHARACTERISTICS OF VS1 AND P18A

1. Morphology

Helical bacteria, loosely undulating (not tightly coiled), about 0.3 micrometers in diameter and 6 to 11 micrometers in length. In stationary phase cultures, many round forms of variable diameter appear and there are fewer spiral forms. The round forms are generally regarded as degenerate and are referred to as "cysts" or "large bodies".

Flagella or axial filaments, which are sheathed, lie between the rigid wall of the protoplasmic cylinder and a triple-layered membrane or outer envelope. The latter envelops the whole organism. The flagella are inserted in groups of 9–13 at each end of the protoplasmic cylinder. Where flagella from the opposing bundles meet, they overlap or interdigitate with one another. Each flagellum has its own insertion disc at its origin in the protoplasmic cylinder.

The organisms exhibit translational motility during the logarithmic phase of growth and have a characteristic undulating, snake-like movement. They are Gram-negative.

2. Cultural (growth) conditions (a) Preferred solid medium. 5% citrated sheep blood agar using, as base, Oxoid No. 2 Blood Agar Base.

(b) Temperature requirement. 37°–42° C. Grows less well at or below 35° C.

(c) Gaseous requirement. Strict anaerobe. Requires 5–10% carbon dioxide in hydrogen, using leak-free anaerobic jars. The "Gaspak" (Becton-Dickinson) or "Gaskit" (Oxoid) systems are satisfactory.

(d) *T. hyodysenteriae* can be grown in liquid medium only in sealed containers under a deoxygenated gas mixture e.g. 5% $CO_2$ in $N_2$, deoxygenated by passage through a heated copper column. The medium needs to be supplemented with serum (e.g. rabbit or foetal calf serum) or with a serum-free medium consisting of bovine serum albumin fraction V plus cholesterol. The advantages of substituting this mixture for serum are (a) the absorption of foreign immunoglobulins to the spirochaete during growth and the possibility of sensitizing vaccinated animals to these immunoglobulins is eliminated (the serum used in the medium is always from species other than pigs); (b) harvesting spirochaetes from liquid medium by filtration (a common practice in large-scale production) is considerably easier with 0.5% BSA V than with 10% serum; (c) the commercially available BSA V is cheaper than rabbit serum, earlier found to be the best type of serum for *T. hyodysenteriae.*

3. Growth chacteristics

The most outstanding characteristic on blood agar is the intense clearing or beta haemolysis surrounding areas of growth. Clearing, which is due to lysis of erythrocytes, is often complete round colonies or streaks of P18A. Haemolysis produced by VS1 is slightly less intense than that produced by P18A or virulent strains of *T. hyodysenteriae* generally.

The amount and the appearance of surface growth on blood agar varies with the moistness of the plates.

In liquid media, the spirochaetes produce a typical swirling growth (streaming birefringence) when shaken. Substantial quantities of gas are produced (the medium contains 0.5% glucose).

4. Physiological properties

| | |
|---|---|
| Indole production | positive |
| Glucose | |
| Fructose | |
| Maltose | acid production |
| Sucrose | |
| Lactose | |
| Trehalose | |
| Mannitol | acid not produced |
| Rhamnose | |
| Esculin | hydrolysed |

Fatty acids produced from glucose (gas-liquid chromatography), mainly acetic and n-butyric acids with traces of propionic, isobutyric and isovaleric acids.

API ZYM-20 tests
positive reactions:
 (2) alkaline phosphatase
 (3) $C_4$-esterase
 (4) $C_8$-esterase lipase
 (11) acid phosphatase
 (14) beta galactosidase
 (16) alpha glucosidase
 (17) beta glucosidase
negative reactions:
 (5) $C_{14}$-lipase
 (6) leucine arylamidase
 (7) valine arylamidase
 (8) cystine arylamidase
 (9) trypsin
 (10) chrymotrypsin
 (12) phosphoamidase
 (13) alpha galactosidase
 (15) beta glucuronidase
 (18) N-acetyl-beta glucosaminidase
 (19) alpha mannosidase
 (20) alpha fucosidase 5. Serological relationship of VS1 to other isolates of *T. hyodysenteriae*

(a) Isolates of *T. hyodysenteriae* may be identified by agglutinin-absorption.

For example, *T. hyodysenteriae* strain VS1 can be distinguished from *T. hyodysenteriae* strain P18A by agglutinin-absorption. If hyperimmune rabbit antiserum against VS1 is absorbed with P18A until, at a dilution of 1/10, it no long agglutinates P18A, the absorbed serum still agglutinates VS1. Conversely, when P18A antiserum is absorbed with VS1 until, at a dilution of 1/10, it no longer agglutinates VS1, the absorbed serum still agglutinates P18A.

It follows that a strain antigenically identical to VS1 should absorb all agglutinins from VS1 antiserum so that the latter would no longer agglutinate either strain. Conversely, antiserum to that strain, when absorbed with VS1 should no longer agglutinate either strain.

(b) Within the species *T. hyodysenteriae*, a number of different serotyes exist, distinguished by their lipopolysaccharides (LPS) which can be extracted with hot, aqueous phenol (Baum and Joens, Infection and Immunity 25, 792–796 (1979)). Using passive haemagglutination and immunodiffusion tests, the LPS of VS1 is distinct from the LPS of P18A and 5 other serotypes of *T. hyodysenteriae* isolated in the UK, the Netherlands, the USA and Canada (R. Lemcke, unpublished observations).

The following are details of the micro-organism deposits of VS1 and P18A, both of which are deposited at the National Collection of Type Cultures, 175 Colindale Avenue, London NW9 5HT, England. VS1 is a patent deposit under the provisions of the Budapest Treaty on the International Recognition of the Deposit of Micro-organisms for the Purposes of the Patent Procedure and therefore subject to availability restrictions, but P18A is available without restriction as from the date of filing this patent application. VS1 was deposited on Feb. 8, 1984 under the number NCTC 11628. P18A was deposited before the date of filing the priority application, under the number NCTC 11615.

Mutants of VS1 can be produced chemically, e.g. using ethidium bromide or acridine orange by irradiation, e.g. using UV light, or by methods employing genetic manipulation. The term "variants" includes biochemical and antigenic variants, as well as variants produced by conjugative processes.

The following Example illustrates the invention.

EXAMPLE

In Experiment I there were 3 groups, each of 9 or 10 4-week old pigs receiving:

(1) Two intramuscular (im) inoculations, given behind the ear, of killed (formalinised) P18A in adjuvant, followed by suspensions of the live avirulent variant VS1 grown on blood agar and administered orally.

(2) Intramuscular inoculation as in (1) of the same formalinised P18A in the same adjuvant, without oral administration of VS1.

(3) No vaccination.

In Experiment II there were 4 groups, each of 10 pigs, namely groups 1, 2 and 3 treated as in Experiment I and, in addition, a fourth group receiving:

(4) Intraperitoneal (ip) inoculation of formalinised P18A in adjuvant followed by the avirulent variant orally.

Experiment III was carried out on six-week old pigs. Batches of 8 pigs (or 7 for Group 3) were given the following treatments:

(1) A "normal regime group" given 2 im injections into the hind leg of killed P18A in adjuvant, and broth cultures of VS1 given orally;

(2) A "parenteral primer group" which were given the same treatment as Group 1 above, with the exception that the animals were given antibiotics 13 days after the first oral dosage with VS1 in order to remove any live spirochaetes before challenge;

(3) An "oral primer group" which were given 3 oral doses of broth cultures of VS1 21, 19 and 13 days before the first im vaccination. Antibiotics were given from 5 days before until the time of im vaccination to remove live VS1 from the pigs;

(4) An "im only group" given 2 im injections;

(5) An unvaccinated group.

In all of these experiments parenteral inoculation was carried out on days 0 and 21. Oral dosage was on days 9, 12 and 33 in Experiments I and II and on days 8, 14 and 16 for Groups 1 and 2 in Experiment III.

The formalinised suspension of P18A was made up as follows. 10 liters of a serum-free broth culture (as described above) of P18A were centrifuged and resuspended in PBS containing 0.2% v/v formalin. The antigen suspension was homogenised with an equal quantity of adjuvant to make an emulsion. The adjuvant used was a mixture of "Marcol 52", (9 parts) and "Arlacel A" (1 part) by volume. The dose administered was 2 ml containing $5 \times 10^9$ organisms in total.

The live organisms of VS1 were cultured on blood agar and the solid medium of 6 well grown blood agar plates was fed to each pig. This was equivalent to at least $10^8$ live organisms per pig. Pigs in Experiment III were given broth culture containing 0.7 to $1.2 \times 10^9$ colony-forming units (c.f.u.) of VS1 per pig.

Challenge

In Experiment I are pigs were challenged by the oral route on two occasions with blood agar cultures of strain P18A, on days 44 and 47. On day 44 the challenge dose per pig was $1.7 \times 10^9$ c.f.u; on day 47 they received $1.0 \times 10^8$ c.f.u. In Experiment II all pigs were challenged 4 times with P18A, viz. twice with blood agar cultures on days 44 and 47 and twice with broth cultures on days 64 and 65. Each pig received challenge doses varying from $5.3 \times 10^8$ to $9.5 \times 10^9$ c.f.u. Pigs in Experiment III were given a larger challenge. They were dosed orally with $2.0 \times 10^{10}$ and $2.8 \times 10^{10}$ c.f.u. on days 49 and 51 respectively.

Post-mortem examination

In Experiment I all surviving pigs were killed on day 82; in Experiment II half of the surviving pigs were killed on day 82 and half on day 89. Experiment III was ended on day 64, i.e. 15 days after challenge, when all pigs showing clinical SD were given antibiotics.

Results

The results of the experiments are summarised in Tables 1 and 2 which follow at the end of the Example. None of the pigs in Experiments I and II which had received the parenteral plus oral regime (im+oral or ip+oral) developed clinical swine dysentery or showed typical SD colonic lesions at autopsy. In Experiment III, where the challenge does was greater, some pigs succumbed to the disease. However the "normal regime group" and the "parenteral primer group" were better protected than the "oral primer group". Parenteral vaccination alone was less effective in preventing clinical swine dysentery and typical clinical colonic lesions.

Autopsy findings associated with vaccination

Sterile abscesses were observed at the site of injection in most pigs which had received im inoculations, and in the lymph nodes draining the abdominal cavity in many that had received ip inoculations.

Mild colonic lesions (indicative perhaps of sub-clinical disease) were observed in all the vaccinated groups (Table 1). However, in Experiment II where 5 pigs of each group were killed 7 days later than the other 5, 7 out of 10 pigs in groups 1 and 2 had mild lesions on day 82, whereas not one of 10 pigs from these groups had lesions on day 89, suggesting that resolution of the lesions may have occurred.

These experiments therefore demonstrate that pigs can be protected against repeated challenge by *T. hyodysenteriae* using a combination of parenteral inoculations of the killed virulent organisms in adjuvant and oral administrations of the live avirulent strain of the bacterium. Moreover Experiments III indicated that the regime of oral priming followed by parenteral injection, was less effective than the parenteral priming followed by oral dosing. Parenteral inoculations of the killed virulent organisms alone did not prevent severe clinical disease following challenge.

TABLE 1

Clinical observations, deaths and autopsy findings in pigs vaccinated in various ways

| Expt. No. | Vaccine regime | Number pigs in group | Number of pigs showing Clinical SD | Death from SD | Typical SD lesions | Mild colonic lesions |
|---|---|---|---|---|---|---|
| I | im + oral | 10 | 0 | 0 | 0 | 0 |
|   | im | 9 | 5 | 0 | 3 | 2 |
|   | none | 10 | 10 | 4 | 10 | 0 |
| II | im + oral | 10 | 0 | 0 | 0 | 4 |
|   | ip + oral | 10 | 0 | 0 | 0 | 3 |
|   | im | 10 | 3 | 0 | 4 | 1 |
|   | none | 10 | 10 | 3 | 10 | 0 |
| III | im + oral | 8 | 2 | 0 | NE | NE |
|   | im + oral* | 8 | 1 | 0 | NE | NE |
|   | oral + im** | 7 | 4 | 1 | NE | NE |
|   | im | 8 | 4 | 0 | NE | NE |
|   | none | 8 | 7 | 0 | NE | NE |

*VS1 removed from the animal by antibiotic treatment before challenge.
**VS1 removed from the animal by antibiotic treatment before im vaccination.
NE = Not examined.

TABLE 2

Effect of different vaccination regimes on mean body weight

| Vaccine regime | Mean daily live weight gain (kg/day) after challenge of pigs surviving to end of Experiment | | |
|---|---|---|---|
|  | Experiment I | Experiment II | Experiment III |
| im + oral | 0.45 | 0.64 | 0.53 |
| im + oral* | ND | ND | 0.58 |
| oral + im** | ND | ND | 0.46 |
| ip + oral | ND | 0.64 | ND |
| im | 0.44 | 0.64 | 0.28 |

TABLE 2-continued

Effect of different vaccination regimes on mean body weight

| Vaccine regime | Mean daily live weight gain (kg/day) after challenge of pigs surviving to end of Experiment | | |
|---|---|---|---|
|  | Experiment I | Experiment II | Experiment III |
| none | 0.26 | 0.23 | −0.07 |

*VS1 removed from the animal by antibiotic treatment before challenge.
**VS1 removed from the animal by antibiotic treatment before im vaccination.
ND = Not done.

I claim:

1. A kit for use in a regime of vaccination in which there is administered parenterally to a pig at least one priming dose of a killed pathogenic *T. hyodysenteriae* effective to stimulate the immune response of the pig to a subsequent dose of a live non-pathogenic strain of *T. hyodysenteriae* and at about the same time or